(12) United States Patent
Zakrzewski

(10) Patent No.: US 7,694,367 B2
(45) Date of Patent: Apr. 13, 2010

(54) MULTIPLE POSITION SUPPORT STRUCTURE

(75) Inventor: Edward Zakrzewski, Carol Stream, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 158 days.

(21) Appl. No.: 11/507,688

(22) Filed: Aug. 22, 2006

(65) Prior Publication Data

US 2008/0047068 A1 Feb. 28, 2008

(51) Int. Cl.
*A61G 7/012* (2006.01)
(52) U.S. Cl. ..................... 5/611; 5/600; 5/616
(58) Field of Classification Search ............. 5/600, 5/601, 611, 614, 616
See application file for complete search history.

(56) References Cited

U.S. PATENT DOCUMENTS

| | | | | |
|---|---|---|---|---|
| 3,203,670 A | * | 8/1965 | Farris | 254/122 |
| 4,451,945 A | * | 6/1984 | Heinz et al. | 5/601 |
| 4,613,122 A | * | 9/1986 | Manabe | 5/601 |
| 4,984,774 A | * | 1/1991 | Zupancic et al. | 5/601 |
| 7,140,055 B2 | * | 11/2006 | Bishop et al. | 5/611 |

* cited by examiner

*Primary Examiner*—Fredrick Conley
(74) *Attorney, Agent, or Firm*—Peter L. Kendall

(57) ABSTRACT

A multiple position support structure is disclosed. The support structure comprising a base, a planar member configured for supporting a patient, a linking assembly connecting the planar member with the base, and an actuator assembly operably connected to the linking assembly and the base for moving the planar member from a first position to a second position. The linking assembly includes a first pair of connecting arms and second pair of connecting arms, each arm being bent at a fulcrum point. The actuator assembly includes a driver means, a screw actuator rotatably connected to the driver means, a driver nut mounted about the screw actuator, and a pull arm pivotably mounted to the driver nut. Rotation of the screw actuator causes linear movement of the driver nut and results the pull arm applying a pulling force to the linking assembly. Extension of the linking assembly causes vertical movement of the planar member.

13 Claims, 9 Drawing Sheets

MULTIPLE POSITION SUPPORT STRUCTURE

BACKGROUND

1. Technical Field

The present disclosure relates generally to patient support systems. More particularly, the present disclosure relates to an improved multiple position support system for diagnostic imaging.

2. Background of Related Art

During many diagnostic procedures, it is necessary to provide a support structure, such as a table, for a patient undergoing the diagnostic procedure. Conventional tables are able to move the patient's body through a variety of positions throughout the diagnostic procedure. Once in a position for the diagnostic procedure, the table must be capable of holding the patient essentially motionless during the time needed to perform the diagnostic procedure. This is especially important during an imaging procedure. Movement of the patient and/or table during the imaging procedure could result in unusable images requiring the imaging procedure to be repeated. Other negative results from patient movement during the imaging procedure include additional time spent repeating the imaging procedure and/or unnecessary patient exposure to radiation from repeating the imaging procedure.

Additionally, the tables used in the imaging procedure should provide comfortable patient support since some imaging procedures require the patient to remain on the table for lengthy periods of time. Alternatively, tables may have additional supporting structures to hold a patient's body in a particular position on the table as dictated by the selected imaging procedure.

Conventional tables for imaging procedures are able to move into a position close to the floor for enabling the patient to easily move into position on its top surface. The table is also positionable to allow a patient to be transferred from a gurney, a stretcher, or a wheelchair. Once the patient is positioned atop the table, an operator adjusts the height of the table for the selected imaging procedure. When the imaging procedure uses a multi-modality imaging device having different fields of view, the table, along with the patient, must be moved from the first field of view to the second field of view before completing the procedure.

Conventional multiple position supports structures include a linkage assembly comprising two pairs of legs arranged in a scissor-like configuration to actuate the raising and lowing of a planar member, or bed (FIGS. 1 and 2). These support structures utilize a drive system that applies direct force to the end of one of the pair of legs in a horizontal direction. The configuration of the scissor mechanism in the extreme down position (FIG. 1) results in a tremendous mechanical disadvantage. Of the total force applied directly to the bottom end of the pair of legs, only a small portion of the applied force is utilized in a vertical direction to deliver lift for the bed. In convention scissor-like configuration a majority of the driving force is dispersed as internal tension. As a result, increased stress is applied to linkage assembly and greater driving forces are required for lifting a patient supported on the bed.

Therefore, it would be beneficial to have a multiple position support structure that utilizes a lift mechanism configured for more efficiently utilizing the applied driving force for lifting the bed.

SUMMARY

A multiple position support structure for supporting a patient is disclosed. The support structure comprises a base, a planar member configured for supporting a patient, a linking assembly connecting the planar member with the base, the assembly including a first and second pair of connecting arms, each arm being bent at a fulcrum point, and an actuator assembly operably connected to the linking assembly and the base for moving the planar member from a first position to a second position.

The first and second pair of connecting arms of the support structure each have a first end and a second end, the first ends being pivotably connected to the planar member and the second ends being pivotably connected to the base. The first ends of the first pair of connecting arms are further slidably mounted to the planar member. The second ends of the second pair of connecting arms are also slidably mounted to the base.

The actuator assembly includes a driver means. The driver means include an electric motor, hydraulic or pneumatic actuator, mechanical crank or belt. The actuator assembly further comprises a screw actuator rotatably connected to the driver means, a driver nut mounted about the screw actuator, and a pull arm pivotably connected to the driver nut and rigidly connected to the second pair of connecting arms through a pivot member. Rotation of the screw actuator causes extension of the linking assembly. Counter rotation of the screw actuator causes retraction of the linking assembly.

The multiple position support structure is configured such that extension of the linking assembly causes the planar member to rise. Conversely, retraction of the linking assembly causes the planar member to lower. The actuator assembly applies a pulling force to the linking assembly. The driver means is pivotably mounted to the base.

The present disclosure further provides a linking assembly for use in a multiple position support structure having a base and a planar member. The linking assembly comprises a first pair of connecting arms, and a second pair of connecting arms, each pair of connecting arms being bent at a fulcrum point. Each pair of connecting arms of the linking assembly has a first end and a second end. The first ends of the first pair of connecting arms are slideably connected to the planar member and the second ends of the second pair of connecting arms are slidable connected to the base. The second ends of the first pair of connecting arms are pivotably mounted to the base and the first ends of the second pair of connecting arms are pivotably mounted to the planar member. The first and second pair of connecting arms are configured to be operably connected to an actuator assembly.

Also provided is an actuator assembly for use in a multiple position support structure having a base and a planar member. The actuator assembly comprises a driver means, a screw actuator rotatably connected to the driver means, a driver nut mounted about the screw actuator and capable of linearly traversing the screw actuator upon rotation of the screw actuator, and a pull arm pivotally connected to the driver nut. Rotation of the screw actuator in a first direction raises the planar member with respect to the base and rotation of the screw actuator in a second direction lowers the planar member with respect to the base.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

DETAILED DESCRIPTION OF PREFERRED EMBODIMENTS

Figure 1:
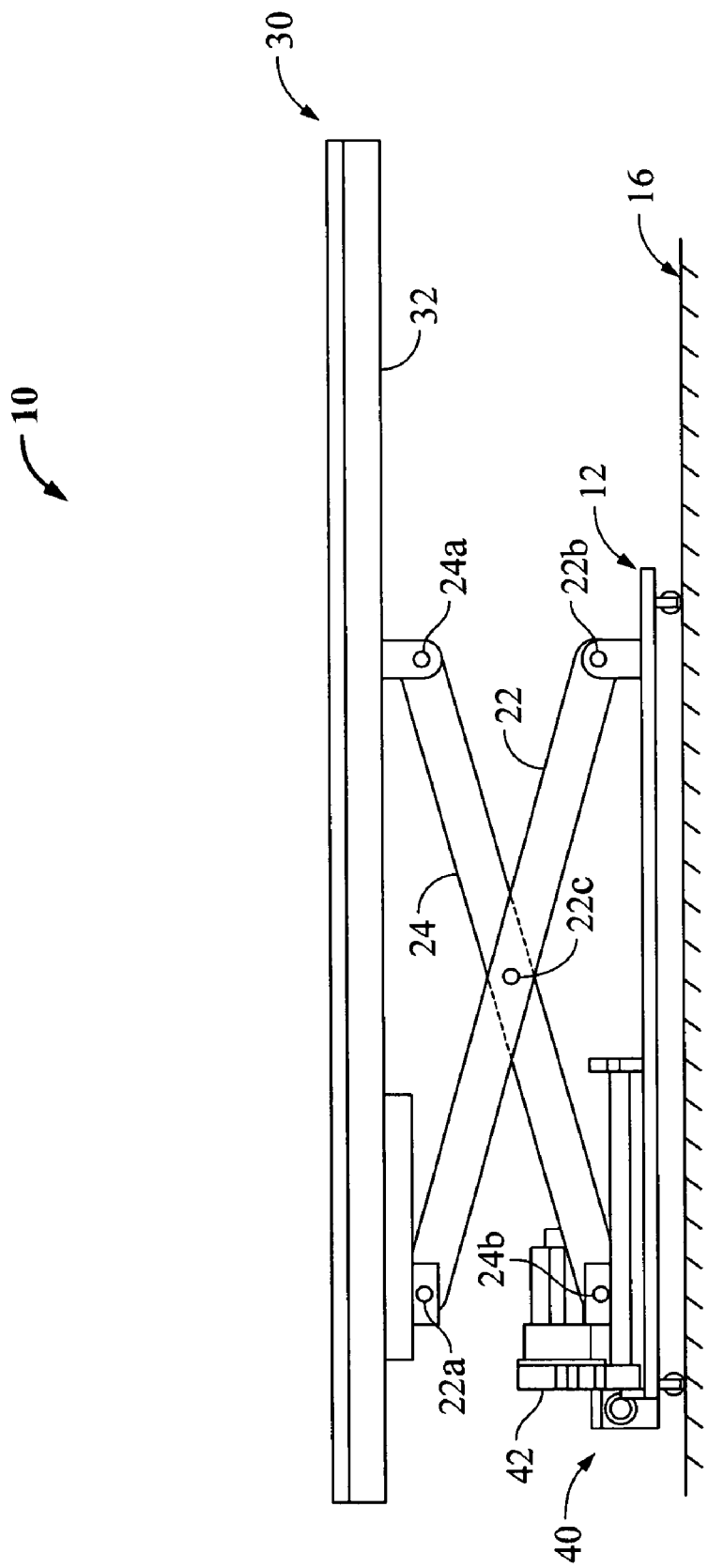
FIG. 1 is a side view of a conventional support structure in a down or lowered position.
Figure 2:
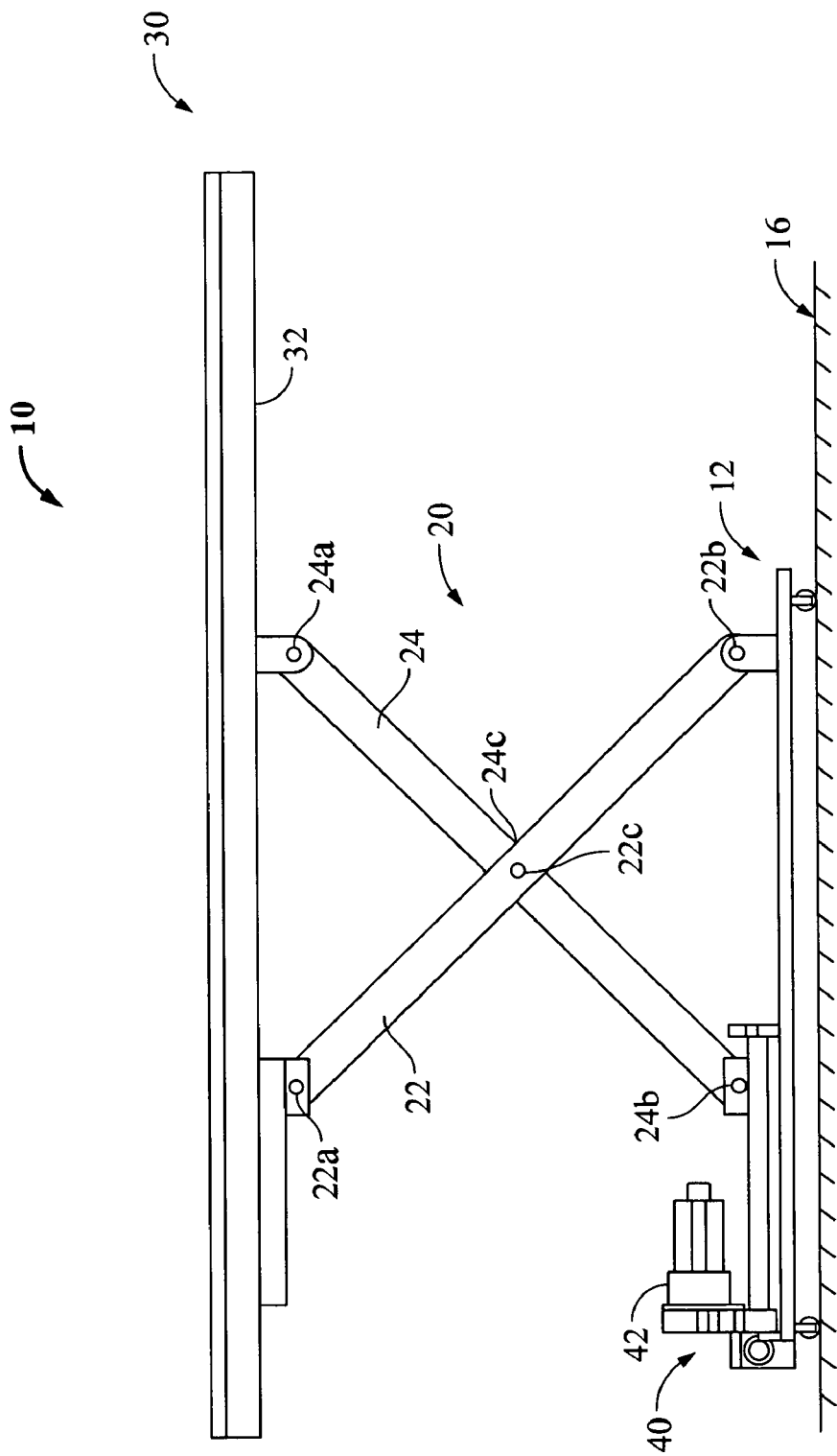
FIG. 2 is a side view of the conventional support structure of FIG. 1 in an up or raised position.

Referring initially to FIGS. 1 and 2, a conventional multiple position support structure utilizing a conventional scissor left mechanism is shown generally as 10. Support structure 10 includes a base 12, a linking assembly 20, a planar member 30, and an actuator assembly 40. Base 12 is configured to be supported on a horizontal surface 16. Linking assembly 20 includes first and second pairs of connecting arms 22,24. Each pair of connecting arms 22,24 form an elongated plate having first ends 22a,24a, second ends 22b, 24b, and fulcrum points 22c,24c located midway between first ends 22a,24a and second ends 22b,24b of connecting arms 22,24, respectively. First ends 24a of connecting arms 24 are pivotally mounted to a bottom side 32 of planar member 30. Second ends 22b of connecting arms 22 are pivotally mounted to base 12. First ends 22a of connecting arms 22 are pivotally and slideably mounted to planar member 30 and second ends 24b of connecting arms 24 are pivotally and slideably mounted to base 12. Actuator assembly 40 is operably connected to second ends 24b of connecting arms 24.

Still referring to FIGS. 1 and 2, conventional multiple position support structure 10 uses actuator assembly 40, including motor 42, to apply direct force to second ends 24b of connecting arms 24. Implementing this configuration, as will be detailed below, is an inefficient use of the driving force.

Figure 3:
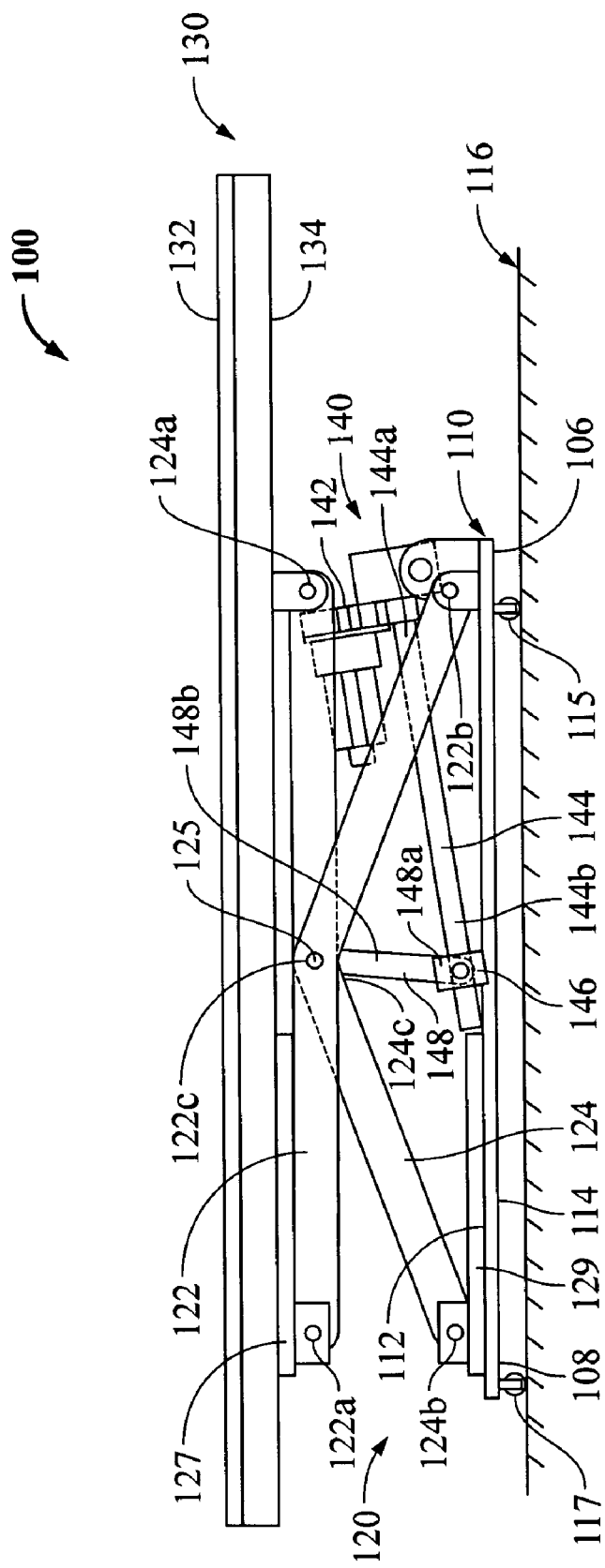
FIG. 3 is a side view of a multiple position support structure constructed in accordance with the present disclosure in a lowered or down position.
Figure 4:
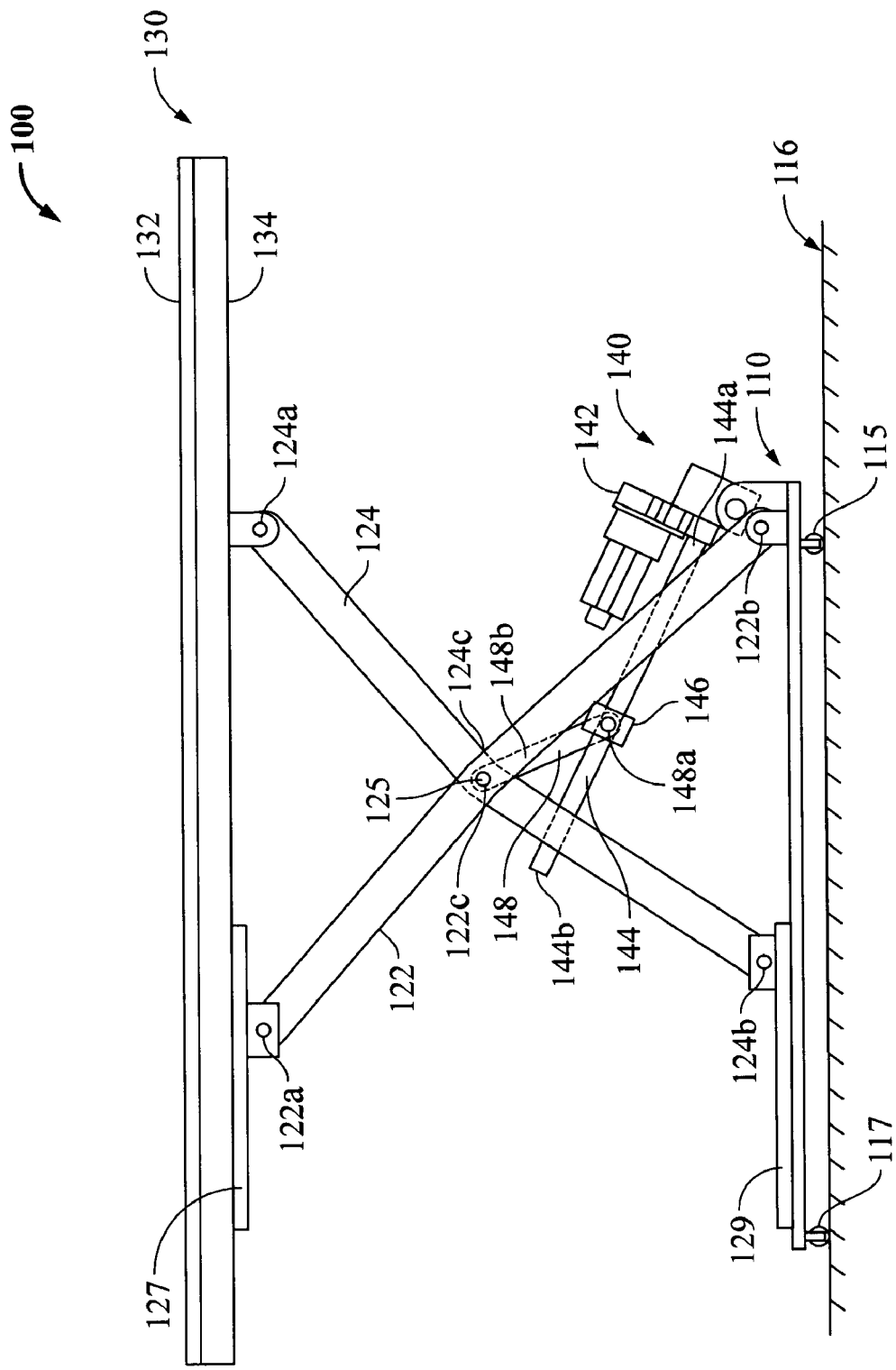
FIG. 4 is a side view of the support structure of FIG. 4 in an up or raised position.
Figure 5:
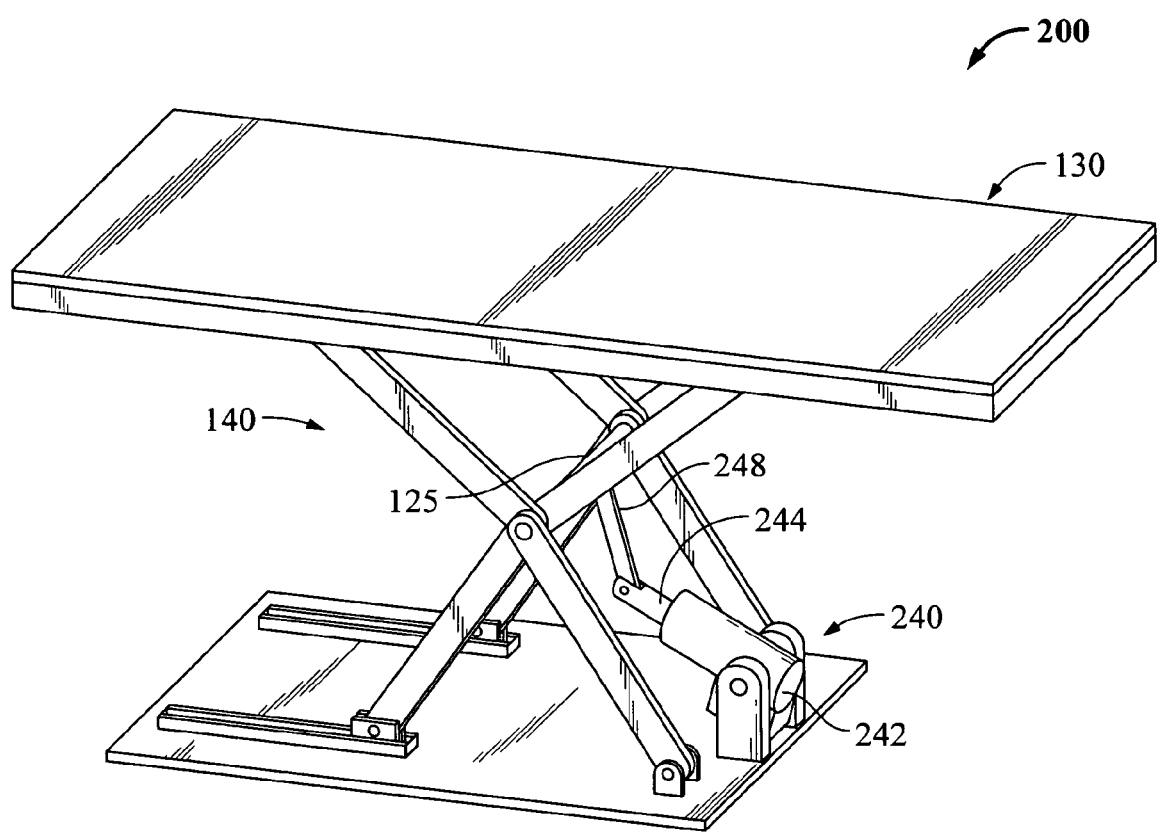
FIG. 5 is a prospective view of an alternate embodiment of the support structure of FIGS. 3 and 4.

Referring now to FIGS. 3-5, preferred embodiments of the present disclosure will be described in detail with reference to the figures. Referring initially to FIGS. 3 and 4, there is illustrated a multiple position support structure, or imaging table, in accordance with the present disclosure and generally designated by reference numeral 100. Multiple position support structure 100 includes a base 110, a linking assembly 120, a planar member 130, and an actuator assembly 140.

Base 110 is an elongate planar structure with a top surface 112 and a bottom surface 114. Base 110 further includes a front-end portion 106 and a back-end portion 108. Base 110 is configured and adapted for placement on a horizontal surface 116 such as a floor. Wheels or casters 115,117 may be included on front-end and/or back-end portions 106,108 of base 110, respectively, to allow for rotation and relocation of support structure 100. Casters 115,117 may include locking mechanism (not shown) for securing support structure 100 in a particular location. Base 110 may further be configured with adjustable legs to vary the distance between base 110 and horizontal surface 116. Non-stick pads may also be applied to base 110 to enable repositioning of support structure 100. In an alternate embodiment, base 110 may be configured to be received within a mount or track positioned on horizontal surface 116 for repositioning support structure 100.

Planar member 130 includes a top surface 132 and a bottom surface 134. Top surface 132 of planar member 130 is configured for receiving and maintaining a patient. Planar member 130 may further include support structures (not shown) for positioning a patient. Planar member 130 may be constructed of metal, plastic or the like, and may also include an assembly for independently rotating and/or angling top surface 132 in relation to base 110.

Linking assembly 120 includes a first and second pair of substantially similar connecting arms 122,124. Each pair of connecting arms 122,124 includes first ends 122a,124a, second ends 122b,124b, and fulcrum points, 122c,124c. Each pair of connecting arms 122,124 are bent or kinked at fulcrum points 122c,124c, respectively. First ends 124a of connecting arms 124 are pivotally mounted to bottom surface 134 of planar member 130. Second ends 122b of connecting arms 122 are pivotally mounted to front-end portion 106 of base 120. First ends 122a of connecting arms 122 are pivotally mounted to bottom surface 134 of planar member 130 using a linear bearing assembly 127. Linear bearing assembly 127 enables first ends 122a of connecting arms 122 to slide horizontally along the length of planar member 130. Second ends 124b of connecting arms 124 are pivotally mounted to back-end portion 108 of base 120 using linear bearing assembly 129. Linear bearing assembly 129 enables second ends 124b of connecting arms 124 to slide horizontally along the length of base 110. A connecting rod 125 extends through fulcrum points 122c,124c of connecting arms 122,124, respectively. Connecting rod 125 is rigidly connected to each pair of connecting arms 122,124. Each pair of connecting arms 122,124 are arranged within linking assembly 120 such that the kink or bend opens downward, or facing base 110.

In the preferred embodiment, actuator assembly 140 includes a driving means 142, a screw actuator 144 operably connected to driving means 142, an actuator driver nut 146 mounted about screw actuator 144, and a pull arm 148 connecting actuator assembly 140 with linking assembly 120. In the present configuration driving means 142 comprises an electric motor, however, driving means 142 may be of any conventional means for applying a force, including but not limited to hydraulics, pneumatics, and manual cranks or belts. Driving means 142 is pivotably mounted to front-end 106 of base 110. Screw actuator 144 includes a first end 144a and a second end 144b. First end 144a of screw actuator 144 is rotatably mounted to driving means 142. Second end 144b of screw actuator 144 comprises a threaded portion (not shown)

for receiving actuator driver nut 146. Actuator driver nut 146 is configured to mount about the second end 144b of screw actuator 144 and is capable linear movement along the length of screw actuator 144 during rotation of screw actuator 144 by driving means 142. Pull arm 148 includes a first end 148a and a second end 148b. First end 148a of pull arm 148 is pivotably mounted to actuator driver nut 146. Second end 148b of pull arm 148 is rigidly connected to connecting rod 125.

Actuator assembly 140 is configured such that in a first, or lowered position (FIG. 3) actuator driver nut 146 is maintained at the distal most end of its travel along screw actuator 144. Rotation of screw actuator 144 by motor 142 causes the linear movement of actuator driver nut 146. As actuator driver nut 146 is pulled along screw actuator 144 pull arm 146 pivots about and exerts a force on connecting rod 125. Connecting rod 125 acts on linking assembly 120 causing extension of connecting arms 122,124. Thus, the lateral movement of actuator driver nut 146 towards motor 142 causes the extension of linking assembly 120 and vertical movement of planar member 130. Counter rotation of screw actuator 144 by motor 142 causes retraction of connecting arms 122,124. The height of planar member 130 in relation to base 110 is determined by the distance actuator driver nut 146 travels along screw actuator 144. Linking assembly 120 is configured such that full extension of connector arms 122,124 is achieved when actuator driver nut 146 reaches its proximal most travel along screw actuator 144. Planar member 130 may be maintained at any height between completely lowered and fully extension.

Referring now to FIG. 5, in an alternate embodiment of multiple position support structure 200, motor 142 is replaced by an actuator 242. Actuator assembly 240 operates in a manner similar to actuator assembly 140, however, instead of actuator driver nut 146 traversing screw actuator 144, a piston 244 is retracted or extended from within actuator 242. Piston 244 is pivotably connected to a pull arm 248 which is pivotably connected to connecting rod 125. As piston 244 is retracted within actuator 242, pull arm 248 exerts a force on connecting rod 125 and linking assembly 140 is extended. Thus, retraction of piston 242 causes planar member 130 to rise. Actuator 242 and piston 244 are configured such that upon full retraction of piston 244 within actuator 242, linking assembly 140 obtains maximum extension. When piston 244 is complete extended from actuator 242, planar member 130 is in the a completely lowered position.

By way of example only, the following discussion will compare in detail the advantage of multiple position support structure 100 over prior art support structure 10 that utilizes a conventional scissor lift mechanism. To more clearly illustrate the forces acting on support structures 10,100, FIGS. 1-4 have been reproduced as FIGS. 6-9, respectively, including the forces acting on the various components and the necessary dimensions for calculating such forces. FIGS. 6-9 do not include reference characters, however, FIGS. 1-4 are identical to FIGS. 6-9 and may be referenced to better understand the following discussion.

Figure 6:
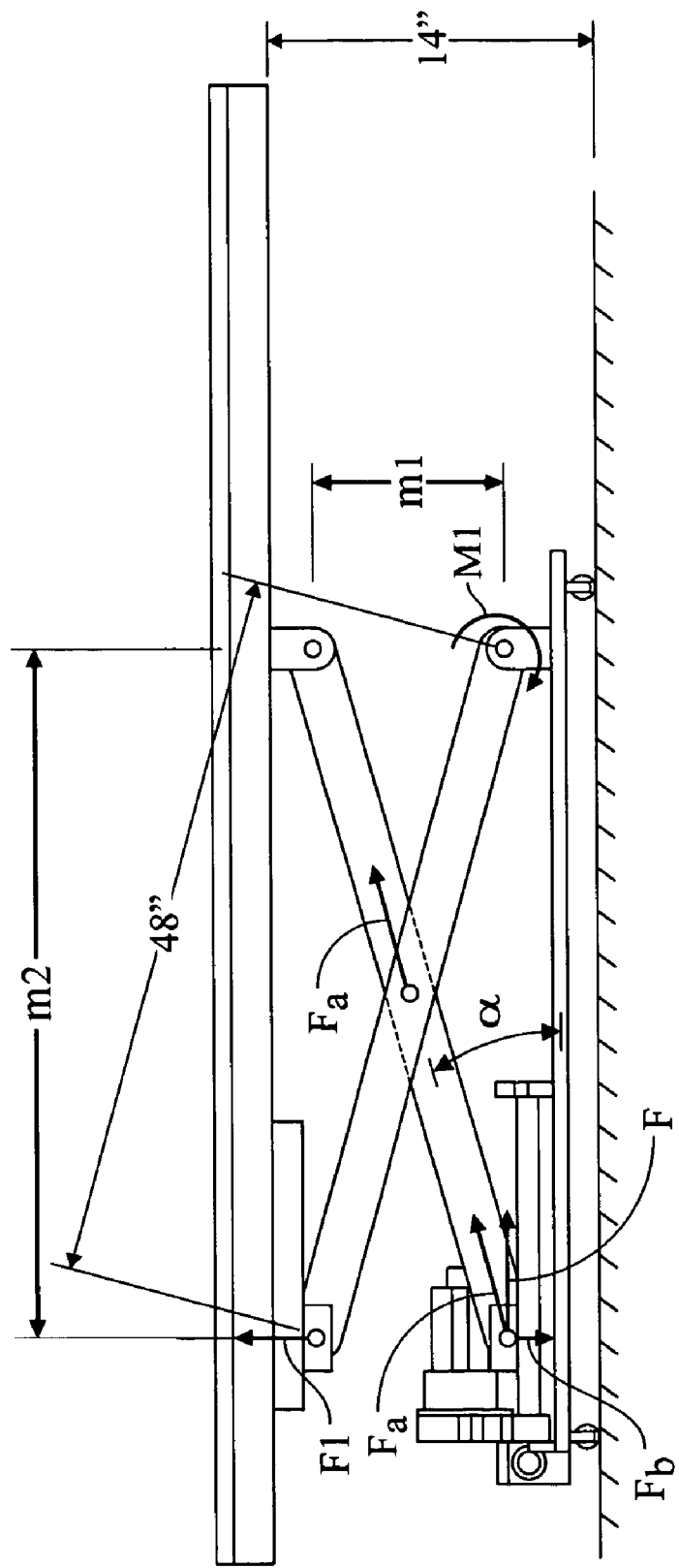
FIG. 6 is a side view of the conventional support structure of FIGS. 1 and 2 illustrating the forces acting upon support structure when in a down or lowered position.

Referring initially to FIGS. 1 and 6, support structure 10 is shown in a lowered, or down, position. The distance between bottom surface 32 of planar member 30 and horizontal surface 16 is 14 inches. Connecting arms 22,24 are symmetrical and are 48 inches in length. A first angle $\alpha$ formed between base 12 and second connecting arm 24 measures 10°. An applied force F supplied by motor 42 of actuator assembly 40 is applied directly to second end 24b of leg 24 in a horizontal direction. In this and the following examples, an exemplary applied force F of 1,500 lbs. is delivered by actuator assembly 40. Applied force F can be resolved into a first force Fa and a second force Fb. First force Fa works along connecting arm 24 while second force Fb works in the direction of base 12. First force Fa works on fulcrum point 24c of connecting arm 24 and creates a first moment M1 around second end 22b of connecting arm 22. First force Fa equals applied force F divided by the cosine of first angle $\alpha$ (Fa=F/cos $\alpha$=1500 lbs/cos 10°=1523 lbs). First moment M1 is equal to first force Fa times a first moment arm m1, or the distance between second end 22b of connecting arm 22 and first end 24a of connecting arm 24. First moment arm m1 equals 8.20 inches, therefore, first moment M1 equals 12,490 in.-lbs. (M1=F× m1=1,523 lbs×8.20"=12,490 in.-lbs). First lifting force F1 is calculated by dividing first moment M1 by a second moment arm m2, or the horizontal distance between first end 22a of connecting arm 22 and first end 24a of connecting arm 24. Second moment arm m2 is 47.27 inches. Therefore, first lifting force F1 equals 264 lbs. (F1=12,490 lbs./47.27"). The maximum force available for support structure 10 utilizing the conventional scissor lift mechanism in the down position is 264 lbs.

Figure 7:
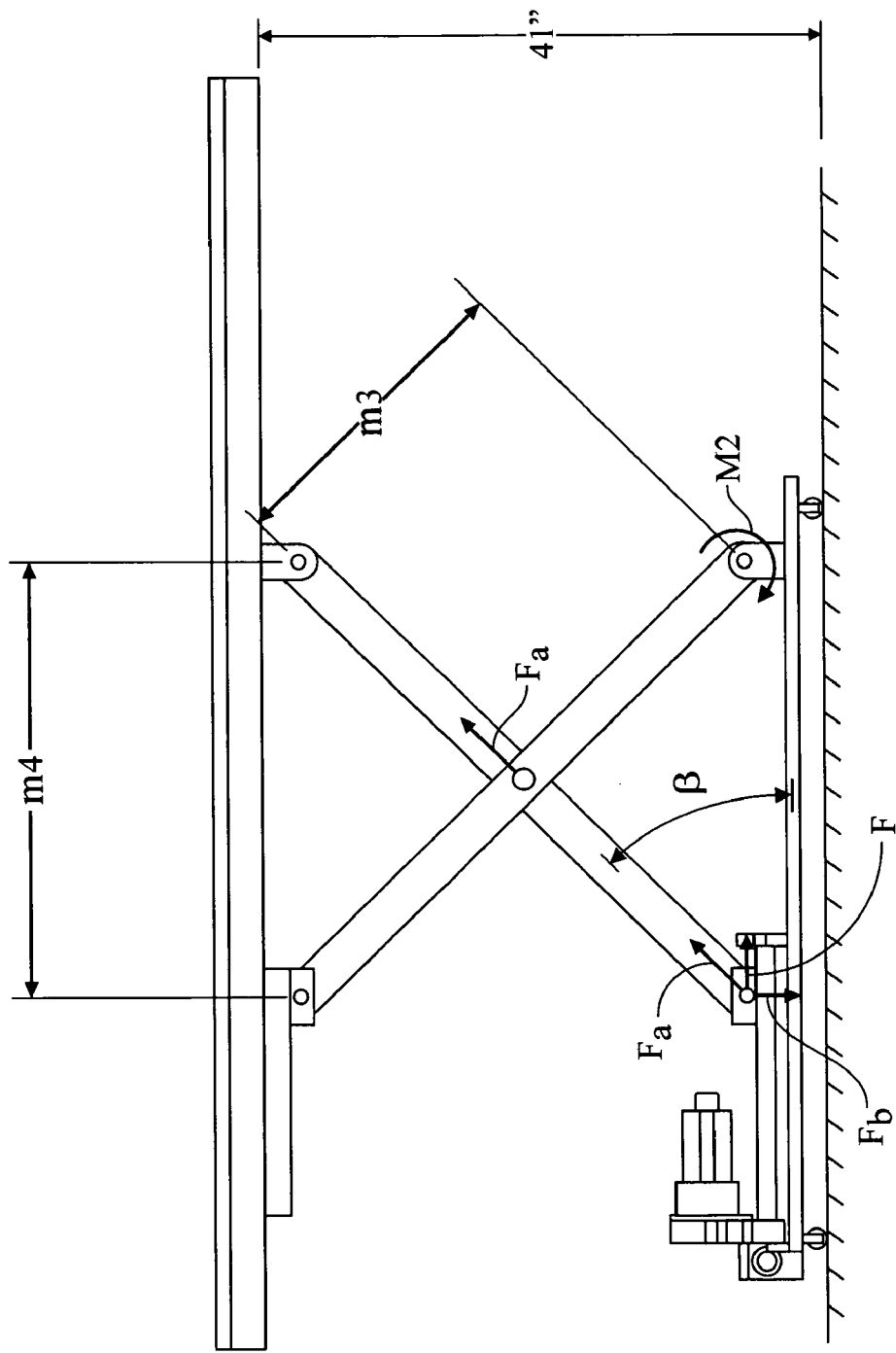
FIG. 7 is a side view of the conventional support structure of FIGS. 1 and 2 illustrating the forces acting upon support structure when in an up or raised position.

Referring now to FIGS. 2 and 7, support structure 10 is shown in a raised, or up, position. In a raised position, the distance between bottom surface 32 of planar member 30 and horizontal surface 16 measures 41 inches. A second lifting force F2 for support structure 10 in a raised position can be calculated in a manner similar to that previously performed to calculate first lifting force F1. In the raised position a second angle $\beta$ formed between second connecting arm 24 and base 12 measures 44°. First force Fa is calculated as above, using the same driving force F. First force Fa equals 2,085 lbs. (Fa=F/cos $\beta$=1,500 lbs/0.7193=2,085 lbs). A second moment M2 is formed about second ends 124b of connecting arms 124 with a third moment arm equaling 23.92 in. Thus, M2 equals 49,879 in.-lbs. (M2=Fa×m3=2,085 lbs.×23.92 in.=49,879 in.-lbs.) Second lifting force F2 is calculated by dividing second moment M2 by a fourth moment arm m4, or the distance between first end 122a of connecting arm 122 and first end 124a of connecting arm 124. Therefore, in a raised position lifting force F2 equals 1,535 lbs. (F2=M2/m4=49,879 in.-lbs/ 32.49 in.=1,535 lbs.). The maximum force available for support structure 10 utilizing the conventional scissor lift mechanism in the up position is 1,535 lbs.

With the maximum force available for support structure 10 in the up position being higher than the force in the down position, support structure 10 is assured of a sufficient power lever for the entire travel of planar member 30. As is seen by this example, the lifting power deficit is mainly pronounced in the down position. Multiple position support structure 100 address this power deficit by implementing pull arm 148 at fulcrum point 122c,124c of connecting arms 122,124, respectively, and raising this joint up toward planar member 130. Pull arm 148 provides extra lifting moment in addition to the advantageous angular direction of the pulling force.

Figure 8:
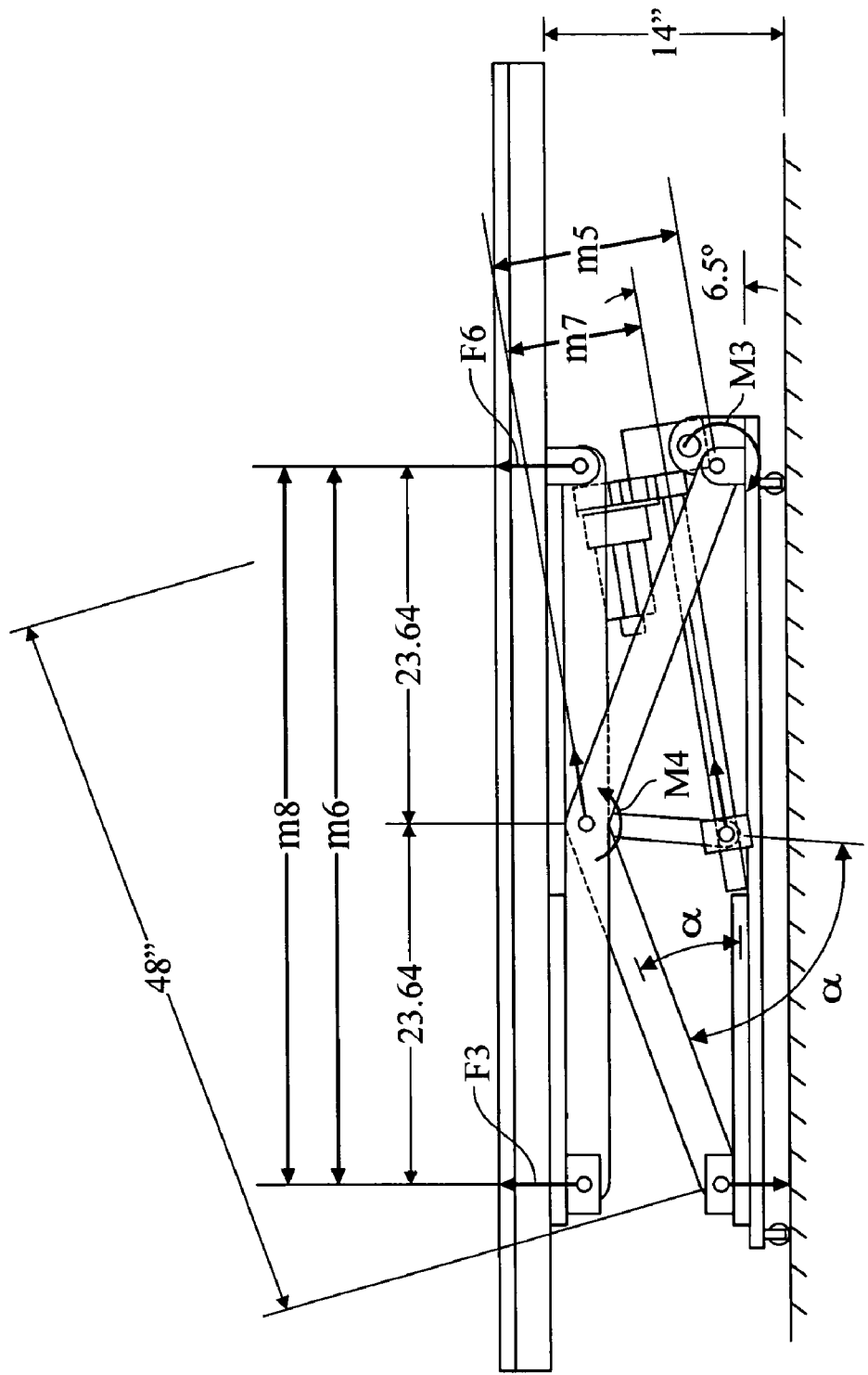
FIG. 8 is a side view of the multiple position support structure of FIGS. 3 and 4 illustrating the forces acting upon support structure when in a down or lowered position.

Referring now to FIGS. 3-4 and 8-9, the maximum force available for multiple position support structure 100 will calculated in a manner substantially similar to that of conventional support structure 10. Referring initially to FIGS. 3 and 8, support structure 100 is shown in a lowered, or down, position. The distance between bottom surface 134 of planar member 130 and horizontal surface 116 remains the same as above, measuring 14 inches. Connecting arms 122,124 retain a length of 48 inches, however, unlike connecting arms 22,24, connecting arms 122,124 are uneven and asymmetrical in that they are kinked or bent off center at fulcrum points 22c,24c, respectively. This modification causes fulcrum points 122c, 124c of linking assembly 130 to be moved up 3.5" as compared with the location of fulcrum points 22c,24c of linking assembly 20, each in a down position. This modification also changes first angle α formed between base 110 and second connecting arm 124 from 10° to 18°. Pull arm 148 is attached at an angle γ relative to second connecting arm 124. Actuator assembly 140 is further angled at 6.5° relative to horizontal plane 116.

A third moment M3 is created about second end 124b of second connecting arm 124. Third moment M3 is equal to applied force F times a fifth moment arm m5, or the relative distance between second end 122b of connecting arm 122 and fulcrum point 122c of connecting arm 122. Fifth moment arm m5 equals 10.30 inches, therefore, third moment M5 equals 15,450 in.-lbs. (M3=F×m7=1,500 lbs.×10.30"=15,450 in.-lbs). A third lifting force F3 is calculated by dividing third moment M3 by a sixth moment arm m6, or the horizontal distance between first end 122a of connecting arm 122 and second end 124b of connecting arm 124. Sixth moment arm m6 measures 47.27 inches, therefore, third lifting force F3 equals 327 lbs. (F5=15,450 lbs/47.27"=327 lbs.).

Still referring to FIGS. 3 and 8, a fourth lifting force F4 creates a fourth moment M4 about fulcrum point 124c from applied force F. Seventh moment arm m7 of fourth moment M4 measures 8.53 inches. Thus, fourth moment M4 equals 12,795 in.-lbs. (M4=F×m7=1,500 lbs.×8.53"=12,795 in.-lbs.). Fourth lifting force F4 is calculated by dividing fourth moment M4 by a eighth moment arm m8, or the distance between first end 122a of connecting arm 122 and first end 124a of connecting arm 124. Eighth moment arm m8 measures 47.27 inches, therefore, fourth lifting force F4 equals 271 lbs. (F4=15,450 lbs./47.27 in.=271 lbs.). The maximum force available for support structure 100 in the down position is the sum of third lifting force F3 and fourth lifting force F4, or 598 lbs. (Ftotal=F3+F4=327 lbs.+271 lbs.=598 lbs.).

The increase in total force available for lifting of support structure 100 over conventional support structure 10 is represented by ratio E between the total force available for each support structure 100,10. Thus, ratio E of total increase in force capacity, Ftotal/F2, equals 2.27, or an increase in force capacity of 127% (E=598 lbs./264 lbs.).

Figure 9:
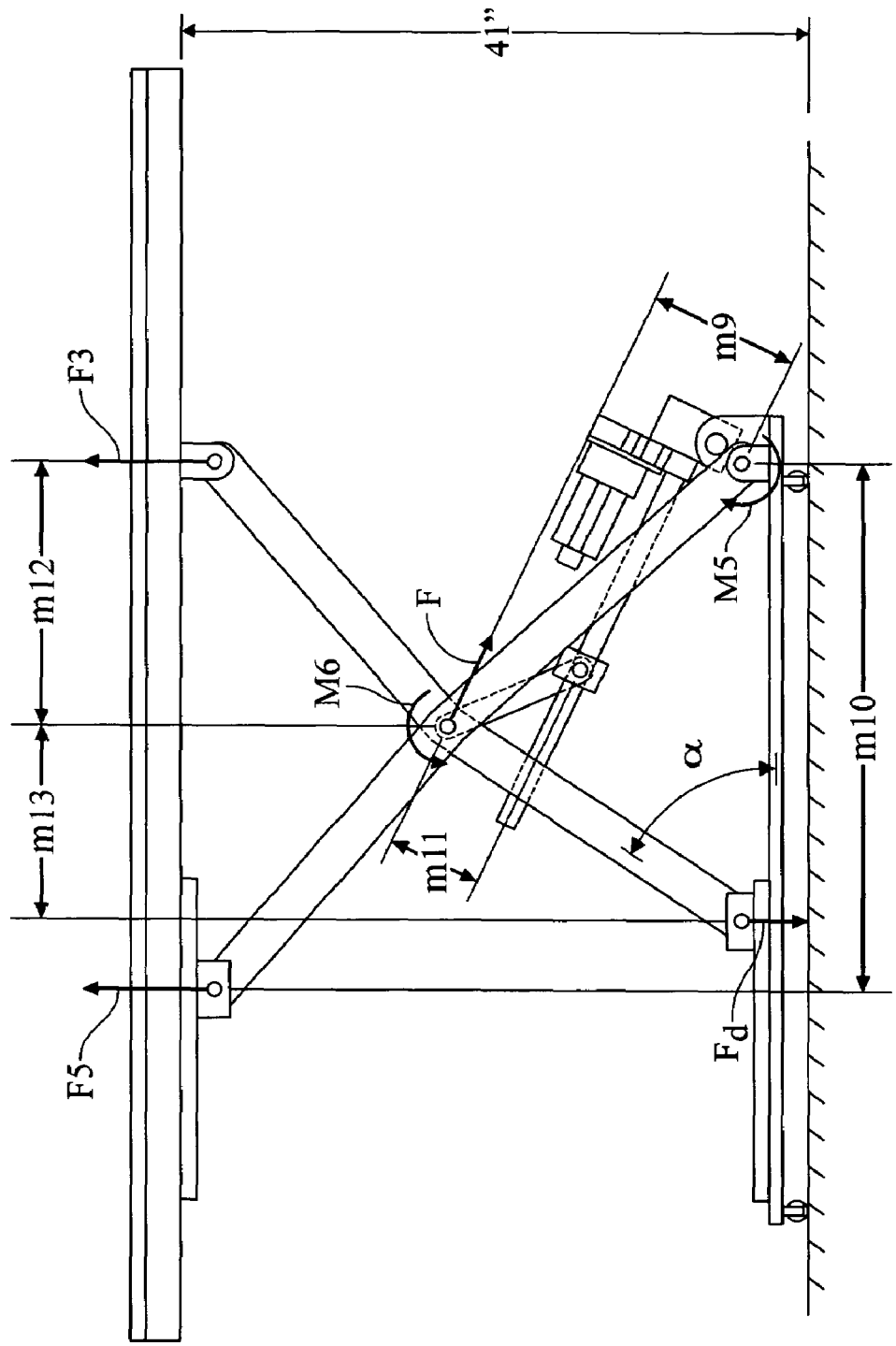
FIG. 9 is a side view of the conventional support structure of FIGS. 3 and 4 illustrating the forces acting upon support structure when in an up or raised position.

Referring now to FIGS. 4 and 9, support structure 100 is shown in a raised, or up, position. The distance between bottom surface 134 of planar member 130 and horizontal surface 116 remains the same as above, measuring 41 inches. The calculation of force for lifting of support structure 100 in its raised position is substantially similar to the above calculations for support structure 100 in a lowered position. A fifth moment M5 is created about second end 122b of second connecting arm 122. Fifth moment M5 is equal to applied force F times a ninth moment arm m9, or the relative distance between second end 122b of connecting arm 122 and fulcrum point 122c of connecting arm 122. Ninth moment arm m9 equals 9.19 inches, therefore, fifth moment M5 equals 13,785 in.-lbs. (M5=F×m9=1,500 lbs×9.19-=13,785 in.-lbs). A fifth lifting force F5 is calculated by dividing fifth moment M5 by a tenth moment arm m10, or the horizontal distance between first end 122a of connecting arm 122 and second end 122b of connecting arm 122. Tenth moment arm m10 measures 32.49 inches, therefore, fifth lifting force F5 equals 424 lbs. (F3=13, 785 lbs./32.49"=424 lbs.). Thus, 424 lbs. of force is available for support structure 100 from actuator assembly 140 applied to second end 122b of connecting arm 122.

Still referring to FIG. 5, a sixth lifting force F6 creates a sixth moment M6 about fulcrum point 124c by applied force F. An eleventh moment arm m11 of sixth moment M6 measures 4.63 inches. Thus, sixth moment M6 equals 6,945 in.-lbs. (M6=F×m10=1,500 lbs.×4.63"=6,945 in.-lbs.). Sixth lifting force F6 is calculated using the moment equation around the fulcrum point 122c of connecting arm 122. Thus, sixth moment M6 is equal to the sum of sixth lifting force F6 times a twelfth moment arm m12, or the horizontal distance between first end 124a and fulcrum point 124c of connecting arm 124, and third force Fd times a thirteenth moment arm m13, or the horizontal distance between second end 124b and fulcrum point 124c of connecting arm 124. Twelfth moment arm m12 equals 18.37 inches and thirteenth moment arm equals 14.12 inches, therefore, sixth lifting force F6 is 188 lbs. (M6=F6×m12+Fd×m13=F6×18.37"+Fd×14.12"=F6×18.37"+1.3010 F6×14.12"=36.8672 F6; F6=188 lbs.). Thus 188 lbs. of force is available for support structure 100 from actuator assembly 140 applied to fulcrum point 122c of connecting arm 122. The maximum force available for support structure 100 in the raised position is the sum of fifth lifting force F5 and sixth lifting force F6, or 612 lbs. (Ftotal=F5+F6=424 lbs.+188 lbs.=612 lbs.). Thus, the total lifting force Ftotal available for lifting support structure 100 in the raised position is 612 lbs. This value is higher than the required force at the down position and as such assures a sufficient power level for the entire vertical travel of planar member 130.

Thus, it should be understood that various changes in form, detail and operation of the multiple position support structure of the present disclosure may be made without departing from the spirit of the present disclosure.

What is claimed is:

1. A structure for supporting a patient comprising:
a base;
a planar member configured for supporting a patient;
a linking assembly connecting the planar member with the base, the assembly including a first and second pair of connecting arms, each arm being bent at a commonly shared coaxial fulcrum point; and
a driver;
an actuator assembly operably connected to the linking assembly and the base for moving the planar member from a first position to a second position,
wherein the actuator assembly further comprises a screw actuator rotatably connected to the driver, a driver nut mounted about the screw actuator, and a pull arm pivotably connected to the driver nut and rigidly connected to a pivotable connecting rod, said connecting rod is connected to said first and second pair of connecting arms at each pair's fulcrum point, wherein said connecting rod defines a longitudinal pivotal axis extending coaxially through each pair's fulcrum point, such that as driver nut is rotated and moved along said screw actuator, said pull arm pivots about the longitudinal pivotal axis and exerts a force on said connecting rod.

2. The structure for supporting a patient of claim 1, wherein the first and second pair of connecting arms each have a first end and a second end, the first ends being pivotably connected to the planar member and the second ends being pivotably connected to the base.

3. The structure for supporting a patient of claim 2, wherein the first ends of the first pair of connecting arms are further slidably mounted to the planar member.

4. The structure for supporting a patient of claim 2, wherein the second ends of the second pair of connecting arms are further slidably mounted to the base.

5. The structure for supporting a patient of claim 1, wherein the driver is pivotably mounted to the base.

6. The structure for supporting a patient of claim 1, wherein the driver is selected from the group consisting of an electric motor, hydraulic or pneumatic actuator, and mechanical crank or belt.

7. The structure for supporting a patient of claim 1, wherein retraction of the linking assembly causes the planar member to lower.

8. The structure for supporting a patient of claim 1, wherein rotation of the screw actuator causes extension of the linking assembly.

9. The structure for supporting a patient of claim 8, wherein counter rotation of the screw actuator causes retraction of the linking assembly.

10. The structure for supporting a patient of claim 1, wherein extension of the linking assembly causes the planar member to rise.

11. An actuator assembly for use in a multiple position support structure having a base and a planar member connected by a first and a second pair of connecting arms having respective commonly shared coaxial fulcrum points, the actuator assembly comprising:
   a driver;
   a screw actuator rotatably connected to the driver;
   a driver nut mounted about the screw actuator and capable of linearly traversing the screw actuator upon rotation of the screw actuator;
   a pull arm pivotally connected to the driver nut and rigidly connected to a connecting rod;
   a screw actuator rotatably connected to the driver;
   a driver nut mounted about the screw actuator; and
   a pull arm pivotably connected to the driver nut,
   wherein said connecting rod is connected to said first and second pair of connecting arms at a first and at a second fulcrum point defined by the first and second pair of connecting arms, respectively, wherein said connecting rod defines a longitudinal pivotal axis extending coaxially through said first and second fulcrum points, such that as said driver nut is rotated and moved in a first direction along said screw actuator, said pull arm pivots about the longitudinal pivotal axis and exerts a force on said connecting rod causing extension of said connecting arms, thereby moving said planar member away from said base.

12. The actuator assembly of claim 11, wherein rotation of the screw actuator in a first direction raises the planar member with respect to the base and rotation of the screw actuator in a second direction lowers the planar member with respect to the base.

13. A structure for supporting a patient comprising:
   a base;
   a planar member configured for supporting a patient;
   a linking assembly connecting the planar member with the base, the assembly including a first and second pair of connecting arms, each arm having a commonly shared coaxial fulcrum point; and
   a driver for causing generally linear displacement;
   an actuator assembly operably connected to the linking assembly and the base for moving the planar member from a first position to a second position, the actuator assembly having a pull arm pivotably connected to the driver and rigidly connected to a pivotable connecting rod, said connecting rod being connected to said first and second pair of connecting arms at each pair's fulcrum point, wherein said connecting rod defines a longitudinal pivotal axis extending coaxially through each pair's fulcrum point, such that as the driver is linearly displaced, said pull arm pivots about the longitudinal pivotal axis and exerts a force on said connecting rod.

* * * * *